United States Patent [19]

Perlin

[11] 4,353,250

[45] Oct. 12, 1982

[54] CALIBRATION DEVICE FOR MICROSURGICAL CLIPS

[75] Inventor: Alfred R. Perlin, Highland Park, Ill.

[73] Assignee: Metatech Corporation, Northbrook, Ill.

[21] Appl. No.: 223,310

[22] Filed: Jan. 8, 1981

[51] Int. Cl.³ .............................................. G01L 5/00
[52] U.S. Cl. .................................. 73/161; 73/862.53; 73/862.54
[58] Field of Search ................ 73/161, 862.01, 862.53, 73/862.54, 849, 856, 860

[56] References Cited

U.S. PATENT DOCUMENTS 3,285,065 11/1966 Ragen et al. .......................... 73/161
4,157,033 6/1979 Shereda et al. ....................... 73/161
4,167,112 9/1979 Ressler ................................. 73/161

Primary Examiner—Charles A. Ruehl
Attorney, Agent, or Firm—Ledig, Voit, Osann, Mayer & Holt, Ltd.

[57] ABSTRACT

A machine for calibrating clips used for clamping blood vessels during surgery. First and second heads are arranged in a frame in opposed relation for relative separating movement from a start position in which the heads are bottomed together. The presented adjacent ends of the heads have registering hooks oriented transversely and parallel to one another, each of the hooks having an adjacent clearance opening for receiving the jaw of an inserted clip. An insertion stop is positioned behind the hooks for limiting the degree of insertion. A drive is interposed between one of the heads and the frame for separating the heads by a predetermined increment thereby to spread the jaws of an inserted clip by a reference amount. A force transducer is interposed between the remaining head and the frame for producing an electrical signal which depends upon the reaction force corresponding to the reference separation. A read-out is provided for the electrical signal for giving direct indication of the clamping strength of the clip. In the preferred form of the invention the drive is in the form of a lead screw actuated by a stepping motor, and a selector is provided to apply a predetermined number of impulses to the motor corresponding to the desired degree of separation. The insertion stop has a plurality of steps indexable into position for establishing different limits of jaw insertion. A "thickness" stop in the second head, adjusted for jaw thickness, maintains the inserted jaw snugly seated against the adjacent hook.

9 Claims, 11 Drawing Figures

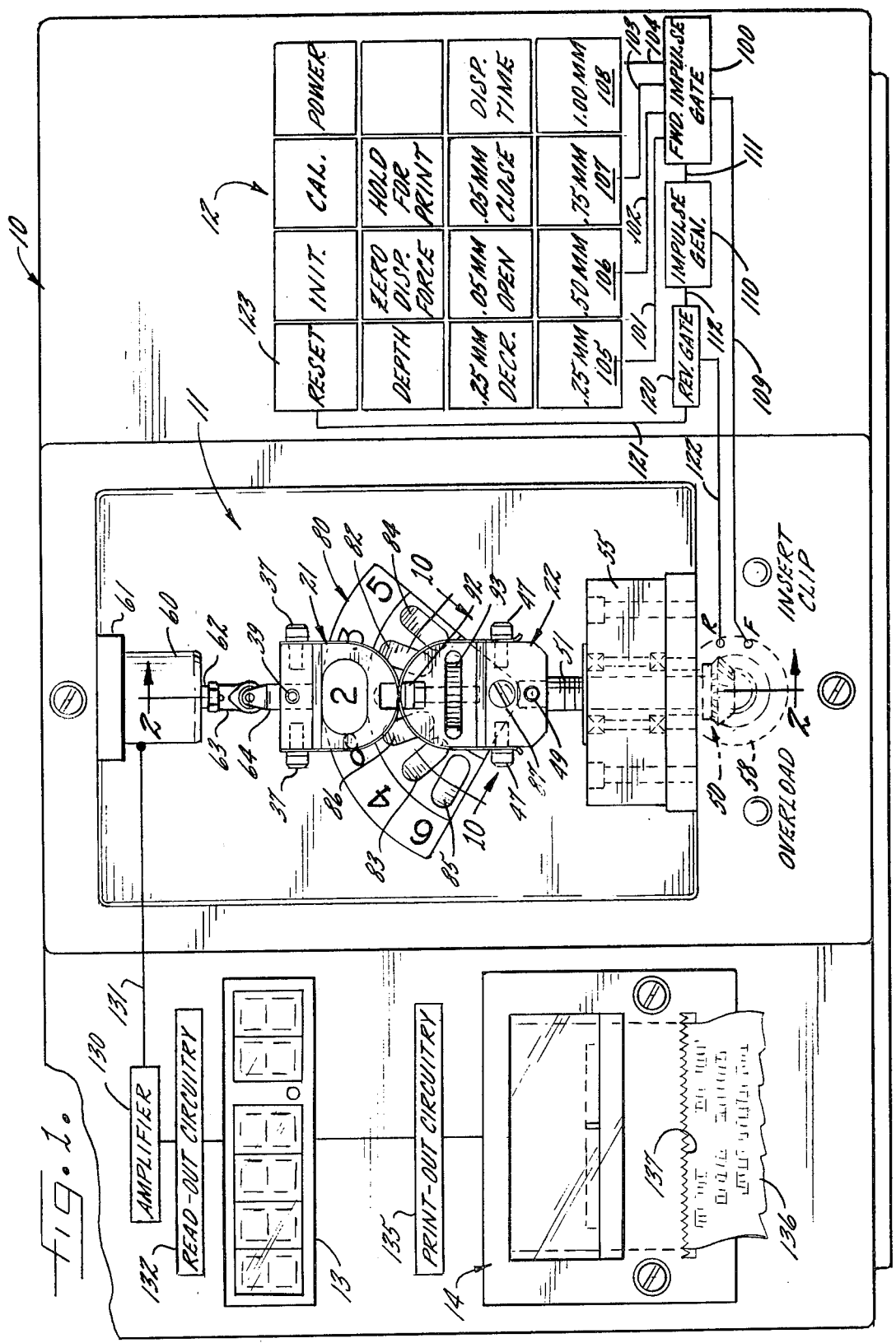

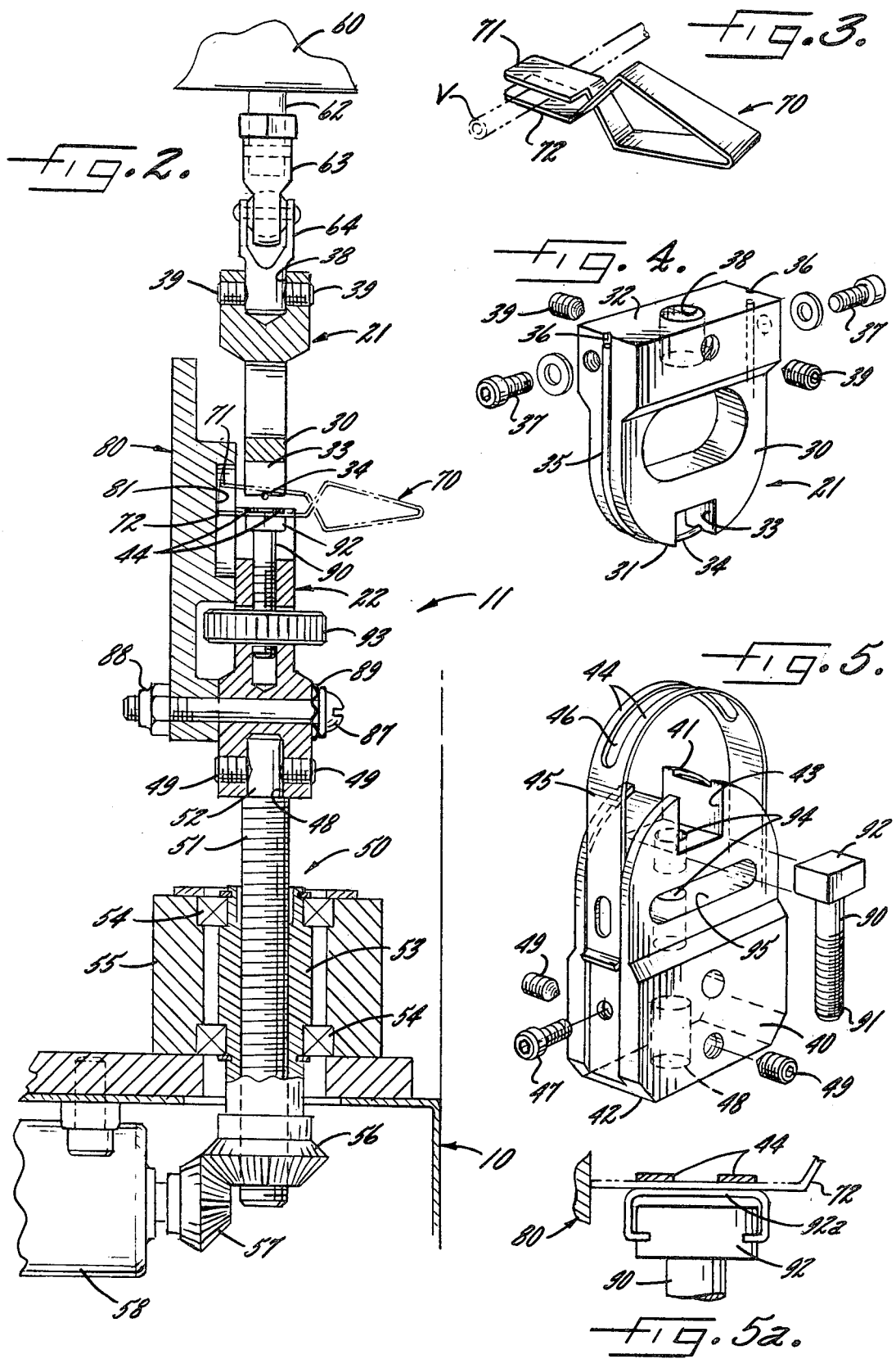

CALIBRATION DEVICE FOR MICROSURGICAL CLIPS

Most surgical procedures involve the clamping of blood vessels. Some blood vessels are large such as those supplying the major limbs while some blood vessels are small and delicate, such as those found in the brain. Surgical clips must be selected having a clamping force suited to the task to assure positive stoppage of the flow in the case of a large blood vessel and to avoid risk of trauma in the case of a small blood vessel, damage which may interfere with subsequent suturing or which may induce a thrombosis with possible fatal effect.

Since the clamping force is so critical individual calibration of each clip prior to use is indicated. In the case of a new clip the calibration may be performed by the supplier. Surgical clips are usually not disposable, and indeed quite expensive, so that the practice has been to sterilize and re-use such clips. Where this is done a clip should be calibrated prior to re-use because of the possibility that the clip may have been strained beyond the elastic limit or otherwise misused or its characteristics affected by the sterilizing operation.

It is an object of the present invention to provide a clip calibrator which is highly accurate and reliable and which is usable with clips having a wide range of size and resilient characteristics. It is another object of the present invention to provide a calibrator for surgical clips which is quick and easy to use and in which dependable results may be obtained even with an inexperienced or unskilled operator. It is a related object to provide a calibration device for clips in which the calibration is unaffected by careless or improper insertion of the clip into the device, provided only that full insertion occurs.

It is a more specific object of the invention to provide a calibrating machine which requires only the setting of a pair of stops to accommodate the machine to clips of different size plus the insertion of a clip into a receptacle and the pressing of an appropriate button on a control panel to obtain prompt read-out and print-out of clamping strength. Thus it is an object to provide a machine which gives a written record of clamping strength on a small slip of paper providing proof positive either where the clip is calibrated at point of use or where the calibration slip is packaged with the clip for later use.

Other objects and advantages of the invention will become apparent upon reading the attached detailed description and upon reference to the drawings in which:

FIG. 1 is a front elevational view of a calibrating machine constructed in accordance with the present invention.

FIG. 2 is a vertical section taken through the center of FIG. 1 and as viewed along line 2—2 therein.

FIG. 3 is a perspective view of a typical clip calibrated in the present machine.

FIGS. 4 and 5 are partially exploded views showing the first and second heads used in the machine.

FIG. 5a is a fragment showing use of a spring as a thickness stop.

Figure 6:
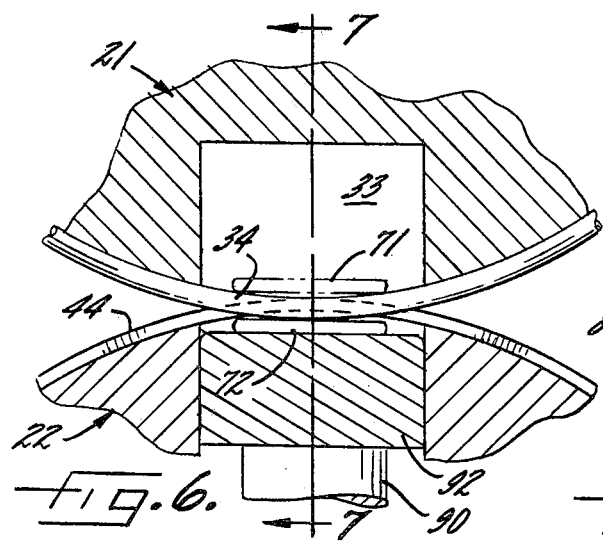
FIG. 6 is an enlarged fragment showing the heads bottomed together in start position.

While the invention has been described in connection with a preferred embodiment, it will be understood that I do not intend to be limited to the particular embodiment shown but intend, on the contrary, to cover the various alternative and equivalent constructions included within the spirit and scope of the appended claims.

Turning to FIG. 1 there is shown a calibrating machine having a housing or frame 10 mounting a stressing and transducer assembly 11 having a control panel 12, a visual read-out 13 and a print-out device 14.

The stressing and transducer assembly 11, into which the clip is inserted for calibration purposes, is shown, in vertical section, in FIG. 2 where it will be noted that the heart of the device is to be found in first and second heads 21, 22 which are arranged in the frame in opposed relation for relative separating movement from a start position in which the heads are bottomed together. Taking first the head 21, which is illustrated in detail in FIG. 4, it includes a body 30 having a presented end 31 and an upper, or mounting portion 32. The presented end has a notch 33 forming an upper clearance space. The notch is bridged by a hook in the form of a cross member 34 which serves to engage the upper one of the jaws of the clip. The cross member 34 is the central section of a length of wire 35 which is recessed in an encircling groove 36 and the ends of which are held in place by clamping screws 37. For securing the head to a suspension member an opening 38 is provided at the upper end accessible, for locking purposes, by set screws 39.

Arranged below the first head 21 is a second head 22 having a body 40, a presented upper end 41, a base portion 42 and with a notch 43 in the upper end. The notch is bridged by a hook 44 in the form of a spaced pair of parallel cross members of thin cross section formed of a strap 45, the central portion of which is slotted at 46, the strap being secured in operating position by clamping screws 47. An opening 48 is formed in the underside of the second head for attachment to the driving means, the opening being in communication with a pair of set screws 49.

In carrying out the invention the heads are mounted in the frame so that the upper and lower hooks in the form of cross members 34, 44 are in register and oriented transversely parallel to one another so that, in the starting position in which the heads are bottomed together, the hook 44 is in straddling relation to the hook 34.

Means are provided for separating the heads by a predetermined increment from the start position thereby to spread the jaws of an inserted clip a predetermined reference amount. In the present instance the drive assembly, indicated at 50, includes a lead screw 51, the upper end 52 of which is of reduced section and received in the opening 48 in the lower head, securely clamped therein by the set screws 49. The lead screw is threaded into a rotatable bushing 53 mounted in bearings 54. The bearings 54 hold threaded bushing 53 captive with respect to a pedestal 55. At its lower end the bushing is connected to a bevel gear 56 which meshes with another bevel gear 57 at right angles thereto and which is secured to a shaft of a stepping motor 58. It will be apparent, then, that by applying a predetermined number of impulses to the stepping motor 58 the threaded bushing is rotated to produce a predetermined small downward movement of the lower head 22, thereby spreading the clip a reference amount.

For the purpose of measuring the reaction force corresponding to reference separation, a force transducer is interposed between the upper head and the frame of the machine. The transducer produces an electrical signal which depends upon the reaction force exerted by the clip as a result of its resilient spreading. Thus there is interposed between the upper head and the frame a transducer 60 having a base 61, which is mounted on the frame, and a plunger 62. In order to insure that the plunger is subjected only to straight line movement the plunger has an associated universal joint consisting of an upper member 63 and a lower member 64, with the latter being anchored, by set screws 39, in the opening 38 in the upper head.

One type of spring clip which is capable of being calibrated by the present device is illustrated at 70 in FIG. 3. Such clip is of unitary construction presenting a pair of jaws 71, 72 of duck bill type which in use are clamped to shut off flow of blood from a blood vessel V.

Figure 10:
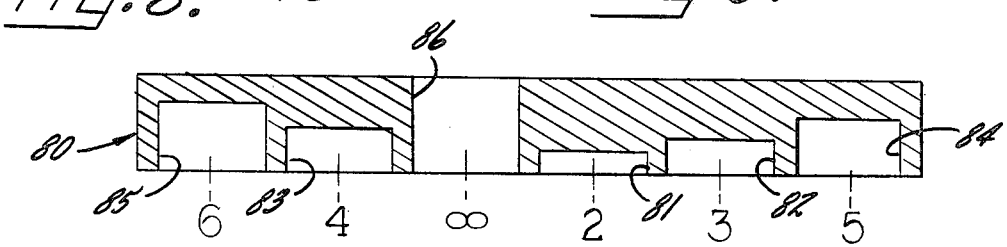
FIG. 10 is a fragmentary section looking along line 10—10 in FIG. 1 and showing the steps in the insertion stop.

In accordance with one of the aspects of the present invention an insertion stop 80 is provided behind the hooks 34, 44 for limiting the degree of insertion of the jaws into the hooks so that the hooks engage the jaws at a position about midway along the length of the latter. For the purpose of accommodating clips of different size the stop member has a set of steps providing stop surfaces of progressive depth as indicated at 81–85 (see FIG. 10) together with a through-opening 86. The insertion stop member 80 is indexably secured with respect to the heads for selection of a predetermined one of the steps. This is accomplished by making the stop member of sector shape (see FIG. 1) and by pivoting it at its lower, or pointed, end to the base portion 42 of the lower head. This is simply accomplished by means of a pivot screw 87 having a nut 88 and with friction being generated in a spring washer 89. It is a simple matter, then, to adapt the insertion stop to a clip of particular size to establish the appropriate degree of insertion: By applying fingertip pressure to one side or the other of the stop member the appropriate one of the surfaces 81–85 may be brought into alignment with the hook position.

In accordance with one of the aspects of the present invention an adjustable "thickness" stop is provided in the notch, or clearance opening, of the second head for snugly retaining the inserted jaw flatly seated against the hook 44 and to restrain the hook against rocking movement during the time that the clip is undergoing calibration. In the present instance the thickness stop is in the form of a screw 90 having a shank 91 and a head 92, the head being preferably of square profile for mated reception in the notch 43 in the lower head. For adjusting the position of the screw 90 a thumbwheel 93 is provided. The lower head is bored as indicated at 94 to provide clearance for the shank of the screw and, in addition, is transversely slotted as indicated at 95 to accommodate the thumbwheel.

In making the thickness adjustment a clip is inserted into the device as illustrated in FIG. 2 and placed under slight tension by drawing the heads apart which seats the jaw 72 on the underside of the hook 44. The thumbwheel 93 is then turned to advance the head of the screw 90 upwardly until it strikes the underside of the jaw 72 following which it is backed off to a slight degree. This leaves a receiving space of appropriate thickness between the underside of the hook 44 and the top surface of the screw adequate for snug reception of the jaw of the clip while preventing the clip from being inserted at an angle or rocking in a vertical plane which would affect the accuracy of the calibration.

Having understood the mechanical elements which make up the device attention may next be given to the electrical means for driving the stepping motor 58. Circuitry for pulsing a stepping motor is well understood by those skilled in the art so that it suffices to employ a simple block diagram. Impulses are fed to the "forward" terminal F of the stepping motor from the forward impulse gate 100 having control lines 101–104 which are respectively connected to pushbuttons 105–108. The impulses, in desired number, flow to the motor on an output line 109. The impulses controlled by the gate 100 are formed in an impulse generator 110 having output lines 111 and 112. The pushbuttons 105–108, in the present instance, provide stepped separations of one-quarter to a full millimeter. For example, by pressing the button 106, corresponding to half a millimeter, line 102 is energized to instruct the forward impulse gate to pass a number of pulses corresponding to a head separation of half a millimeter, the actual number of impulses, of course, being dependent upon the construction of the motor and upon the pitch of the lead screw.

For the purpose of restoring the lower head 22 to its initial position in which the heads are bottomed together, a reverse gate 120 is provided having a control line 121 and an output line 122, the control line being under the control of a reset button 123. The reverse gate 120, supplied with impulses from the generator 110 via line 112, applies impulses to the "reverse" terminal R of the stepping motor causing it to reverse the motion of the lead screw until the heads are restored to their start condition.

In accordance with one of the aspects of the invention circuitry is provided between the force-transducer 60 and the visual read-out 13 so that the read-out reads directly in conventional units the amount of reaction force exerted by the clip when its jaws are separated the reference amount. Thus transducer 60 is connected to an amplifier 130 via line 131, with the output of the amplifier being fed to the input of read-out circuitry 132 which directly energizes the segments of the read-out indicia. The taking of an electrical analog signal from a transducer and converting it to digital form on a display by means of analog-to-digital circuitry 132 is a matter well within the skill of the art and the exact circuitry need not be set forth.

It is a feature of the invention in one of its aspects that, in addition to producing a visual read-out, there is a print-out of the calibration on a small slip of paper which may be secured to, or packaged with, the clip. Thus printout circuitry 135 is provided which may be coupled to the read-out circuitry 132 for energizing the printer 14, the printed output being available on a slip 136 fed from a supply roll within the printer and which may be torn off along a serrated edge 137.

Figure 7:
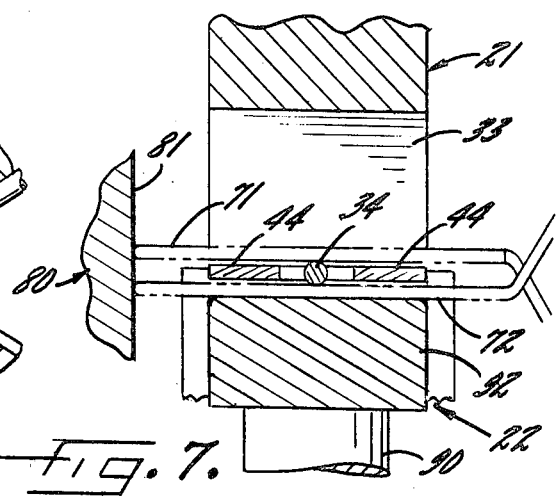
FIG. 7 is a fragmentary section taken along line 7—7 in FIG. 6.

While the construction and operation of the machine will be apparent in view of the foregoing, it will be helpful to consider a typical operating cycle: As a preliminary, the machine is set up to handle a clip of particular size and jaw thickness. First an appropriate one of the stepped stop surfaces 81–85 is moved into a position behind the hooks, a surface being chosen which causes the hooks to be more or less centered along the length of the jaws. To accommodate the jaw thickness and to preclude rocking movement of the clip, the thumbwheel 93 is turned to bring the upper surface of the thickness stop 90 adjacent the underside of the jaw. The position of the heads relative to one another, referred to as the "bottoming" condition, at the time that the clip is inserted as illustrated in FIGS. 6 and 7. Although the term "bottoming" has been used, what is referred to is a start condition of registered alignment between the upper and lower hooks 34, 44 as illustrated in FIG. 7. Bottoming to achieve this condition need not occur between the heads but may occur elsewhere in the system.

Figure 8:
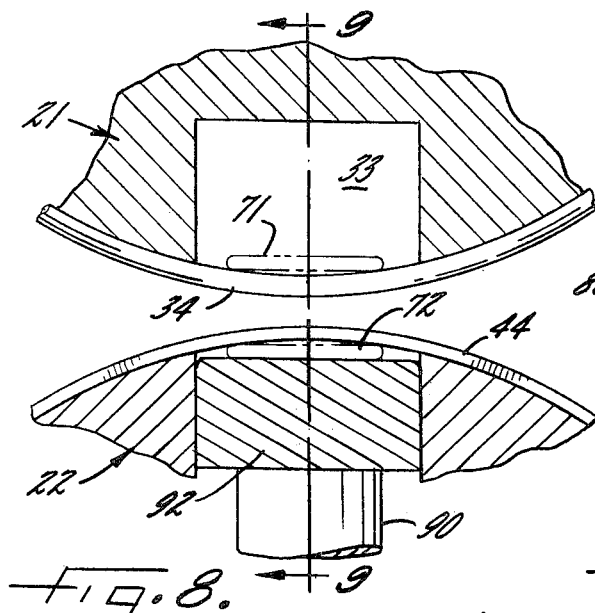
FIG. 8 is an enlarged fragment similar to FIG. 6 but showing the clip spread apart a predetermined reference amount for read-out.
Figure 9:
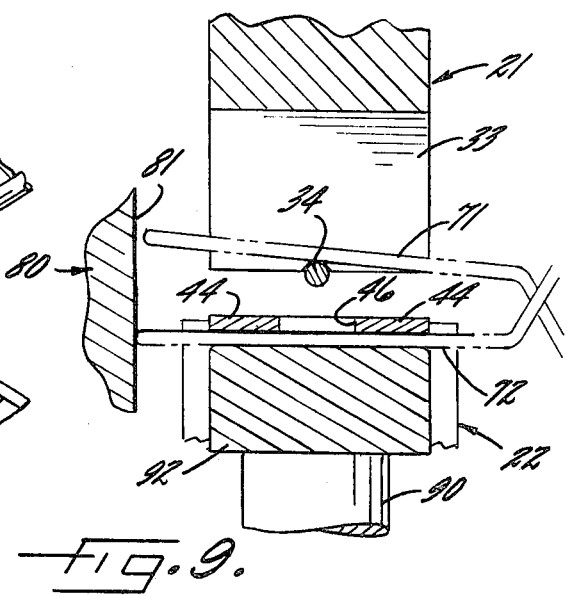
FIG. 9 is a fragmentary section looking along line 9—9 in FIG. 8.

With the clip in place the appropriate one of the buttons 105–108 is pressed to bring about a reference separation for the particular size of clip. Pressing of the pushbutton instructs the forward impulse gate 100 to pass a corresponding number of impulses from the impulse generator to the stepping motor 58 thereby causing rotation of the threaded bushing 53 which, acting upon the lead screw 51, causes lowering of the lower head by the reference amount, as illustrated in FIGS. 8 and 9. The selected spread of the jaws for reference purposes for a given clip construction is preferably in an amount approximating the spread of the jaws in engagement with a blood vessel and in any event is well within the elastic limit of the clip.

The resulting reaction force exerted by the spring clip and detected by the transducer produces a corresponding electrical output signal which, amplified and processed by the read-out and print-out circuitry, provides both a visual and printed indication of the clamping strength of the clip. The reading may conveniently be in terms of grams of force.

It may be noted that one of the benefits of the antirocking feature provided by the thickness stop 90 is that as the jaws are spread apart the upper jaw 71 swings clear of the insert stop surface, for example the surface 81, as indicated by the arrow, so that the insert stop surface does not exert a drag at the tip of the upper jaw which might affect the reading.

The thickness stop 90 discussed above, although it is adjustable to provide a jaw receiving space of a certain thickness dimension is non-yielding. If desired, the thickness stop may be in the form of a yieldable spring which engages the underside of the inserted jaw to press it upwardly against the hook 44. Such a spring, indicated at 92a in FIG. 5a, may be fitted to the head 92 of the screw 90, serving to resiliently press the inserted jaw 72 upwardly against the lower hook 44. Where the range of jaw thickness is limited the spring may be considered as self-adjustable to accommodate variations in thickness and the thumbwheel 93 may, accordingly, be omitted.

The device, as described, is simple and straightforward in construction and operation, and makes use, where possible, of commercially available parts. Almost any drive motor of suitable size and power rating may be employed provided the motor is of the type which steps forwardly or backwardly by a predetermined angular increment upon receipt of electrical pulses of appropriate polarity of which are applied to "forward" and "reverse" terminals, respectively. Similarly, any force-to-signal transducer may be employed which is of appropriate sensitivity and which is capable of producing an electrical output signal which is proportional, in magnitude, to the reaction force of the clip upon being spread apart by a reference amount, or amounts. The read-out and print-out circuitry as well as the circuitry of the impulse generator and its associated gates embody conventional techniques abundantly available to those skilled in the art and hence need not be described in detail.

While additional functions and embellishments of the operation are indicated on the buttons of the control panel 12, such functions may be considered of an optional nature not requiring discussion.

It will be apparent that the objects of the invention set forth above have been amply realized. The device is highly accurate and reliable, usable with clips having a wide range of size and shape, and simple and easy to use even by inexperienced or untrained personnel. The machine may be used at the site of the surgery to enable the surgeon to select a clip of proper calibration for a particular size of blood vessel. In such usage the device is highly economical enabling repeated re-use of clips following sterilization. Alternatively, the calibrating machine may be employed by the manufacturer or supplier of clips with each clip being packaged with its calibration slip from the print-out and with the clips being segregated into groups in accordance with their calibrated clamping force.

While the stressing and transducer assembly 11 is vertically oriented, it may, if desired, be horizontally mounted so that all directional terms used herein should be considered relative.

I claim as my invention:

1. A machine for calibrating surgical clips having a pair of jaws of the duck bill type comprising, in combination, a frame, a first head and a second head in the frame, the heads being arranged in the frame in opposed relation for relative separating movement from a start position in which the heads are bottomed together, the presented adjacent ends of the heads having registering hooks oriented transversely and parallel to one another, the hooks having adjacent clearance openings for receiving respective ones of the jaws, an insertion stop behind the hooks for limiting the degree of insertion of the jaws into the hooks so that the hooks engage the jaws at a reference position about midway along the length of the latter, drive means interposed between at least one of the heads and the frame for separating the heads by a predetermined increment from one another thereby to spread the jaws of an inserted clip a predetermined reference amount approximating the spread of the jaws in engagement with a blood vessel and in any event well within the elastic limit of the clip, a force transducer interposed between at least one of the heads and the frame for producing an electrical signal which depends upon the reaction force of the clip at reference separation, and read-out means responsive to the electrical signal for providing direct indication of the clamping strength of the clip.

2. A machine for calibrating surgical clips having a pair of jaws of the duck bill type comprising, in combination, a frame, a first head and a second head in the frame, the heads being arranged in the frame in opposed relation for relative separating movement from a start position in which the heads are bottomed together, the presented adjacent ends of the heads having registering hooks oriented transversely and parallel to one another, the hook on the first head being in the form of a single cross member of thin cross section, the hook on the second head being in the form of a pair of parallel cross members of thin cross section substantially spaced from one another and in straddling relation to the cross member on the first head when the heads are in start position, an insertion stop behind the hooks for limiting the degree of insertion of the jaws into the hooks so that the hooks engage the jaws at a reference position about midway along the length of the latter, drive means interposed between at least one of the heads and the frame for separating the heads by a predetermined increment from the start position thereby to spread the jaws of an inserted clip a reference amount approximating the spread of the jaws in engagement with a blood vessel and in any event well within the elastic limit of the clip, a force transducer interposed between at least one of the heads and the frame for producing an electrical signal which depends upon the reaction force of the clip at reference separation, and readout means responsive to the electrical signal for providing direct indication of the clamping strength of the clip.

3. A machine for calibrating surgical clips having a pair of jaws of the duck bill type comprising, in combination, a frame, a first head and a second head in the frame, the heads being arranged in the frame in opposed relation for relative separating movement from a start position in which the heads are bottomed together, the presented adjacent ends of the heads having registering hooks oriented transversely in parallel to one another, the hook on the first head being in the form of a single cross member of thin cross section, the hook on the second member being in the form of substantially spaced cross members arranged parallel to one another and straddling the first cross member when the heads are in the start position, the hooks having adjacent clearance openings for receiving the respective ones of the jaws, an insertion stop behind the hooks for limiting the degree of insertion of the jaws into the clearance openings so that the hooks engage the jaws at a reference position about midway along the length of the latter, drive means interposed between at least one of the heads and the frame for separating the heads by a predetermined increment from the start position thereby to spread the jaws of an inserted clip a reference amount approximating the spread of the jaws in engagement with a blood vessel and in any event well within the elastic limit of the clip, a force transducer interposed between at least one of the heads and the frame for producing an electrical signal which depends upon the reaction force of the clip at reference separation, read-out means responsive to the electrical signal for providing direct indication of the clamping strength of the clip, and an adjustable thickness stop in the clearance opening of the second head for snugly maintaining the inserted jaw seated against the hook on the second head and to restrain the clip against inadvertent rocking movement during the separation.

4. The combination as claimed in claim 1 or in claim 2 or in claim 3 in which the presented adjacent ends of the heads have mutually opposed notches formed therein, the hook in the first head being in the form of a wire bridging the notch therein and the hook in the second head being in the form of a thin slotted strap bridging the notch therein, with the slot in the strap in register with the wire when the heads are bottomed together in the start position.

5. The combination as claimed in claim 1 or in claim 2 or in claim 3 in which the insertion stop is adjustable for adjusting the degree of insertion depending upon the size of the clip.

6. The combination as claimed in claim 1 or in claim 2 or in claim 3 in which the insertion stop has a plurality of steps of establishing different limits of jaw insertion and in which the insertion stop is indexably secured with respect to the heads for selection of a predetermined one of the steps.

7. The combination as claimed in claim 1 or in claim 2 or in claim 3 in which the drive means for separating the heads includes a stepping motor with means for applying a predetermined number of impulses thereto corresponding to the desired degree of separation of the heads.

8. The combination as claimed in claim 1 or in claim 2 or in claim 3 in which the drive means for separating the heads includes a lead screw, a stepping motor coupled to the lead screw, and selector means for applying a predetermined number of impulses to the motor corresponding to the desired degree of separation of the heads.

9. The combination as claimed in claim 1 or in claim 2 or in claim 3 in which the read-out means has a printout for producing a printed slip indicating the clamping strength of the clip for packaging with the clip.

* * * * *